United States Patent [19]
Müller et al.

[11] Patent Number: 5,626,876
[45] Date of Patent: May 6, 1997

[54] FLOATING SYSTEM FOR ORAL THERAPY

[75] Inventors: Walter Müller, Neuwied; Edzard Anders, Bornheim, both of Germany

[73] Assignee: LTS Lohmann Therapie-Systeme GmbH & Co., KG, Neuwied, Germany

[21] Appl. No.: 142,843

[22] Filed: Oct. 25, 1993

Related U.S. Application Data

[63] Continuation of Ser. No. 821,269, Jan. 10, 1992, abandoned, which is a continuation of Ser. No. 671,676, Mar. 19, 1991, abandoned, which is a continuation of Ser. No. 427,834, filed as PCT/DE89/00008, Jan. 10, 1989 published as WO89/06956, Aug. 10, 1989, abandoned.

[30] Foreign Application Priority Data

Feb. 5, 1988 [DE] Germany ............... 38 03 382.4

[51] Int. Cl.$^6$ .......................... A61K 9/22; A61M 31/00
[52] U.S. Cl. .................. 424/484; 424/443; 424/464; 424/465; 424/468; 424/489
[58] Field of Search ................. 424/484, 486, 424/489, 443, 464, 465, 468; 604/890.1; 514/960, 962, 963, 964, 965

[56] References Cited

U.S. PATENT DOCUMENTS

| | | | |
|---|---|---|---|
| 3,976,764 | 8/1976 | Watanabe et al. | 424/451 |
| 4,451,260 | 5/1984 | Mitra | 424/444 |
| 4,525,340 | 6/1985 | Lange et al. | 424/424 |
| 4,539,256 | 9/1985 | Shipman | 428/315.5 |
| 4,666,702 | 5/1987 | Junginger | 424/497 |
| 4,764,380 | 8/1988 | Urquhart et al. | 424/465 |
| 4,801,460 | 1/1989 | Goertz et al. | 424/465 |
| 4,814,179 | 3/1989 | Bolton et al. | 424/484 |
| 4,818,542 | 4/1989 | DeLuca et al. | 424/501 |
| 4,830,860 | 5/1989 | Ranade | 424/484 |
| 4,865,789 | 9/1989 | Castro et al. | 264/122 |
| 4,871,549 | 10/1989 | Ueda et al. | 424/466 |
| 4,925,670 | 5/1990 | Schmidt | 424/443 |
| 5,036,057 | 7/1991 | Martin | 514/54 |

FOREIGN PATENT DOCUMENTS 2077585   6/1980   United Kingdom.

OTHER PUBLICATIONS

Wood, A. S. How Improvements in Porous Materials Open Profit Opportunities. Modern Plastics. Feb. 1981, vol. 58, No. 2, pp. 42–43.

Lippold et al. In–Vivo–Prufung einer Multipartikularen Retard–Schwimmarzneiform. European Journal Pharm. Biopharm. 1991, vol. 37, No. 4, pp. 254–261.

Primary Examiner—Melvyn I. Marquis
Assistant Examiner—Robert H. Harrison
Attorney, Agent, or Firm—Kalish & Gilster

[57] ABSTRACT

The invention relates to a floatable, oral, therapeutic system, in which a lengthening of the gastrointestinal residence time of medicaments and a controlled delivery thereof are achieved by systems, which are specifically lighter than the gastric fluid, float on the latter and can only with difficulty reach the lower-lying pylorus, said system using at least one structural element with cavities or voids, such as foams or hollow bodies.

15 Claims, 9 Drawing Sheets

FLOATING SYSTEM FOR ORAL THERAPY

This application is a continuation of Ser. No. 07/821,269, filed Jan. 10, 1992, now abandoned, which is a continuation of application Ser. No. 07/671,676, filed Mar. 19, 1991, now abandoned, which is a continuation of application Ser. No. 07/427,834, filed as PCT/DE89/00008, Jan. 10, 1989 published as WO89/06956, Aug. 10, 1989, now abandoned.

BACKGROUND AND SUMMARY OF THE INVENTION

The invention relates to a floatable, oral therapeutic system. Oral therapeutic systems are active substance-containing means, which deliver the active substances in controlled manner to their environment.

Apart from the problem of controlled active substance delivery, such as is known in connection with the known transdermal, transmucosal, sublingual, nasal, vaginal and transplantable systems, in the case of oral therapeutic systems additional problems occur in connection with keeping the system sufficiently long in the stomach or gastrointestinal tract, the place where the active substance is to be delivered. This so-called gastrointestinal residence time is subject to very significant individual differences and is inter alia dependent on the nutritional habits of the individual.

Attempts have been made to exert an influence on the gastrointestinal residence time of medicaments by increasing the same. Thus, it has e.g. been proposed to use medicament forms, which stick to the stomach and/or intestinal wall (Drug Development and Industrial-Pharmacy, 9(7) 1316–19, (1983). Attempts have also been made to use materials which swell strongly in the stomach and can consequently not pass through the pylorus, so that their large volume brings the stomach into a fed-up state. They suppress the periodically occurring, violent peristaltic movements occurring in the case of an empty stomach and as a result of which larger food particles can pass into the intestine. It has finally been proposed to use for this purpose systems, which are specifically lighter than the gastric fluid, which float on the latter and can only pass with difficulty to the lower lying pylorus.

Thus, e.g. U.S. Pat. No. 4,167,558 describes a floatable tablet, which floats in the gastrointestinal fluid solely as a result of the low specific gravity of its matrix formulation. U.S. Pat. No. 4,055,178 proposes a flat system provided with a floating chamber. U.S. Pat. Nos. 3,901,232 and 3,786,831 describe systems, in which a specifically lower weight leads to inflation in the stomach through the evaporation of a physiologically unobjectionable fluid boiling at a temperature which is below body temperature.

The hitherto known solutions of this problem suffered from serious disadvantages. In the case of U.S. Pat. No. 4,167,558, matrix materials with an adequately low specific gravity must be used, so that only a limited selection is possible. In the case of the flat system of U.S. Pat. No. 4,055,178 provided with a floating chamber, certain geometrical characteristics are predetermined and cannot be obviated. The systems described in U.S. Pat. Nos. 3,901,232 and 3,786,831 have a complicated structure and require high manufacturing expenditure.

The problem of the present invention is therefore to develop novel, floatable, oral therapeutic systems, which do not suffer from the above disadvantages.

This problem is solved by a therapeutic system comprising at least one structural element with cavities, such as foams or hollow bodies.

Further advantageous developments can be gathered from the following description.

It may be advantageous that the structural elements are homogeneously distributed in the system. The structural element can be film-like. The structural element may surround the active substance.

The structural element or elements may have a polymer, such as polyethylene, polypropylene, polyamide, polystyrene, polyester, polyacrylate, polytetrafluoroethylene, polyvinyl chloride, polyvinylidene chloride, copolymers from the monomers on which said polymers are based, or polysiloxane.

It may comprise also an inorganic material, e.g. glass or ceramic material.

In a preferred embodiment of the invention the system comprises a control membrane for active substance delivery.

It may have an active substance-containing hot melt material in which the structural elements are embedded.

The structural element or elements are embedded in an active substance-containing shaped article.

The shaped article can be a hydrogel or it can form a hydrogel on contact with the gastrointestinal fluid.

The system may comprise floatable subsystems, the central parts of which are structural elements with a high cavity proportion, said structural elements being provided with an active substance-containing coating or having active substances.

The subsystems may be enclosed in a capsule soluble under physiological conditions.

The floatable subsystems can be combined by a binder to form a shaped article, whereby optionally the subsystems can be released on contact with the gastric and/or intestinal fluid, which dissolves the binder.

The system may have various layers and at least one layer is a floatable structural element.

The system may be folded or rolled together prior to administration and may unfold or unroll under stomach conditions.

Advantageously the system is completely or partly decomposable under physiological conditions.

It has surprisingly been found that through the use of materials having a high void proportion or gas cavities, it is possible to manufacture oral systems with a low specific gravity. Suitable materials are e.g. foams or hollow spheres, which can be made from the most varied materials, e.g. from all thermoplastic polymers, natural polymers and inorganic compounds, such as glasses and ceramic materials.

In particular foam-like or microporous structures of thermoplastic polymers in the form of powders, film, rods and hoses are commercially available.

The penetration of water into pores can be prevented by an adequately small pore size (by capillary effects) or by the use of hydrophobic polymers, which prevent the access of water, particularly into voids in the interior of polymers, provided that the pore size is sufficiently small.

It is possible to use glass spheres of small diameter, such as are commercially available, as hollow bodies for reducing the specific gravity of the system.

DE-OS 32 15 211 describes a process for the production of microporous powders filled or charged with active substance. In this case, at elevated temperature, a homogeneous polymer solution is atomized into a gas, whereby demixing occurs between the polymer and solvent. After removing the solvent, particles with a microporous structure are left behind. If active substance is added during the production of the microporous particles, or the pore forming agent is itself the active substance, active substance-containing microporous powders are obtained.

EP-A2-0 146 740 discloses a process for the production of shaped articles with a microporous structure from microporous powders using a pressing or compressing process. Possibilities are given for filling or charging the microporous shaped articles with active substances prior to compression.

EP-A2-0 162 492 describes a tablet with a membrane controlling active substance delivery and which is produced from microporous powders by a pressing or compressing process.

The present invention is characterized in that use is made of microporous substances or structures, which have a low specific gravity and which are maintained for a sufficiently long time under the conditions in the stomach. In no case are all the voids of the structural elements filled with active substances. Adequate cavities are always left free to ensure a low specific gravity in order to maintain the floatability of the system.

A particular advantage of the invention is that systems can be filled with active substance by up to 70% by volume and up to 80% by weight. It is also possible to additionally coat the systems filled with active substance with a control coating, e.g. a membrane controlling via the pore size, or a membrane controlling via the diffusion rate, in order to be able to perform further control functions.

BRIEF DESCRIPTION OF THE DRAWINGS

The invention is described in greater detail hereinafter relative to the attached drawings, wherein show:

FIG. 4b A section through a preferred embodiment of a subsystem of FIG. 4a.

FIG. 4c A section through a further preferred embodiment of a subsystem according to FIG. 4a.

DESCRIPTION OF THE PREFERRED EMBODIMENT

Figure 1:
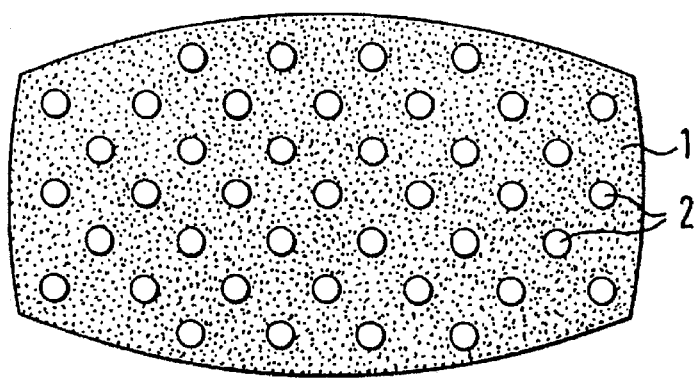
FIG. 1 An oral therapeutic system, in which cavity structural elements 2 are distributed in an active substance-containing matrix 1.

FIG. 1 shows a preferred embodiment of the invention in the form of a so-called skeletal table 1, which comprises a matrix formulation which does not disintegrate or only slowly disintegrates under the physiological conditions in the stomach. It can e.g. be produced in that granular materials are coated and permeated with permeable acrylic resins and the particles are then compressed without additional fillers. In place of acrylic resins, it is also possible to use other, usually high molecular weight adjuvants, which only have a limited solubility in the digestive juices. On admixing with the granular material, prior to compression, an adequate quantity of hollow bodies or foam-like structural element particles 2, the specific gravity of the tablet 1 is lowered to such an extent that it floats in the gastric fluid. It is also possible to produce a tablet in which a crystalline active substance mixed with microporous structural element powders 2 is compressed. It is also possible to provide the active substance particles, prior to compression, separately with control membranes, e.g. diffusion membranes, using per se known processes, such as spraying or the like. The tablets produced according to the invention (cf. FIG. 1) can obviously also contain conventional adjuvants, such as water-insoluble or swellable substances, e.g. cellulose derivatives, polymers, fats, waxes or physiologically unobjectionable hot melt materials. Particularly if such a tablet is produced from a hot melt material, it will have an adequate mechanical strength at ambient temperature or slightly increased temperatures and in this case it can be provided with a coating which dissolves rapidly in the stomach. The active substance escapes from such systems mainly by passive diffusion. Such a system can only be made reliably floatable by adding structural element materials with a high cavity proportion of appropriate size, nature and quantity.

Figure 2:
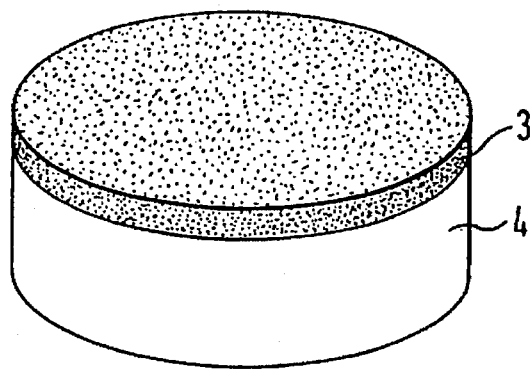
FIG. 2 An inventive multilayered tablet.

FIG. 2 shows a tablet-like therapeutic system, which has two layers, one layer 3 being the microporous structural element, whose function is to make the complete system floatable. This tablet can e.g. be advantageously produced in a single compression process. However, it is also conceivable to produce the two tablet parts separately and then join them together. It is possible to use as the floating aid a punched microporous film portion, which can e.g. be adhesively joined to the active substance-containing system part 4.

Figure 3:
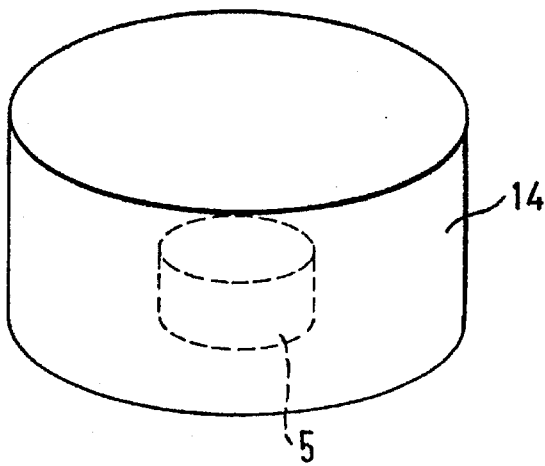
FIG. 3 A tablet-like system with a microporous structural element as the tablet core.

FIG. 3 diagrammatically shows a further tablet-like, oral, therapeutic system, in which a microporous core 5 is provided as a floating aid for the active substance-containing matrix 14 and is surrounded on all sides by it. This tablet can also be advantageously produced in a single tabletting process.

Figure 4A:
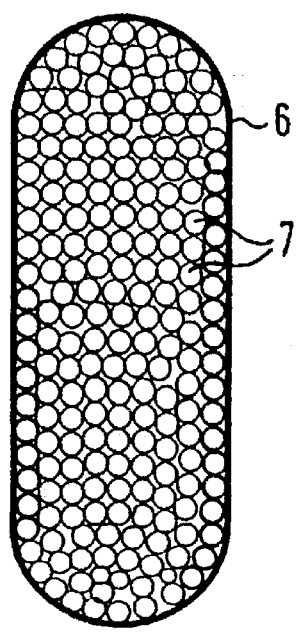
FIG. 4a A system having several subsystems.
Figure 4B:
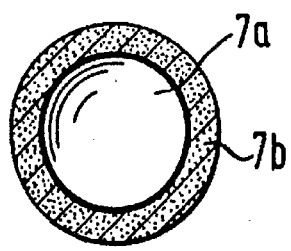
Figure 4C:
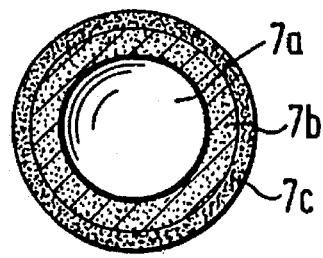

FIG. 4 shows another preferred embodiment of inventive floatable, therapeutic systems, in which a plurality of floatable subsystems are contained in a stomach-soluble capsule 6. Preferred subsystems 7 of the overall system of FIG. 4a are shown in section in FIG. 4b. Core 7a is a roughly spherical hollow body or foam particles, which is provided with an active substance-containing coating 7b. The active substance release in this embodiment of a subsystem 7a can be controlled by means of the composition of the active substance formulation, the thickness of the active substance-containing coating, the overall surface and the active substance concentration. As shown in FIG. 4c, in the case of a further preferred embodiment, in addition to the coating shown in FIG. 4b, a control membrane 7c can be applied.

Instead of using a capsule as a container for the subsystem 7, it is also possible to join the subsystems by a stomach-soluble or dissolvable binder, which ensures that the overall system is held together until administration.

Figure 5A:
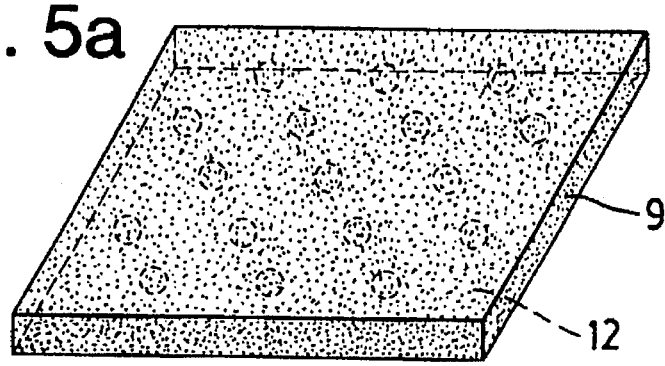
FIG. 5a A flat system.

FIG. 5a shows an inventive, flat system, which e.g. comprises a physiologically unobjectable, void-containing polymer material 12 and adjuvants 9. Prior to application or administration it is e.g. rolled or folded together and can also be packed in a capsule. The active substance is then released by diffusion on administration, or through the polymer being decomposable under physiological conditions. The system is floatable as a result of the incorporated voids or cavities.

Figure 5B:
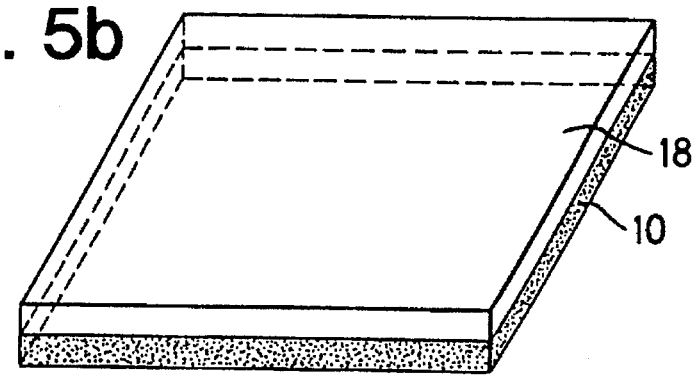
FIG. 5b A multilayer system, in which one layer is constituted by the structural element.

FIG. 5b shows a two-layer laminate, in which coating 18 has cavities and functions as a floating aid. It is preferably a film, which has a high cavity proportion as a result of its foam-like structure, whereas coating 10 is an active substance-containing matrix. It is obviously also possible to provide further layers of different composition without passing beyond the scope of the invention.

Figure 6A:
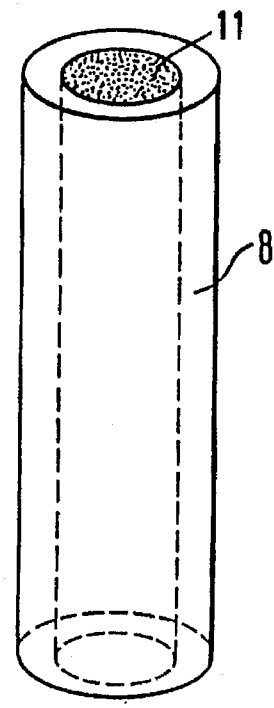
FIG. 6a An intermediate for producing the system shown in FIG. 6b.

FIG. 6a shows a tubular structure with a cavity-containing film 8 as a tubular material, which circularly surrounds an active substance-containing matrix material 11, which is provided in the tube.

Figure 6B:
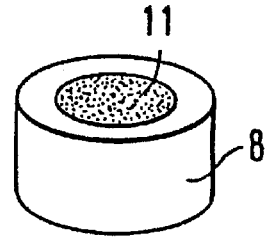
FIG. 6b A further preferred therapeutic oral system, in which the floatable structural element surrounds in circular manner an active substance-containing preparation.

The active substance-containing material 11 can e.g. be introduced into a hot melt material or the like and the system can subsequently be cut into the disks shown in FIG. 6b. The systems shown in FIG. 6b can obviously have in per se known manner additional controlling membranes or other jacket materials dissolving in the stomach and/or can be surrounded by the same.

Thus, according to the invention it is inter alia possible to homogeneously distribute in an overall system structural elements with a high cavity proportion; as a central part of numerous small subsystems; in the form of a film as part of a coating-possessing body; as the central part of a tablet; as part of a multicoating tablet; or as the envelope, so as to make an oral therapeutic system floatable.

Simple, oral, therapeutic systems, in which e.g. the cavity-possessing structural elements are homogeneously distributed in the overall system can be produced by per se known extrusion, injection molding or molding processes. It is also possible to produce such systems by pressing or compressing processes.

A separate production of the active substance-containing part of the tablet and the floating aid is possible and they are then combined to an overall system by bonding and heat sealing. The floating aid, like other parts of the system, can be produced by compression/punching or extruding processes.

EXAMPLE 1

417 g of theophylline coated with 78 mg of an ethylene-vinyl acetate copolymer (commercially available from ICI under the name EVATANE 28.800), are homogenized with 171 mg of polyamide-12 foam (ACCUREL EP 900) and compressed to a constant volume of 0.74 ccm. The density of the pressed article is 0.8 g/ccm and each article contains approximately 420 mg of theophylline.

Figure 7:
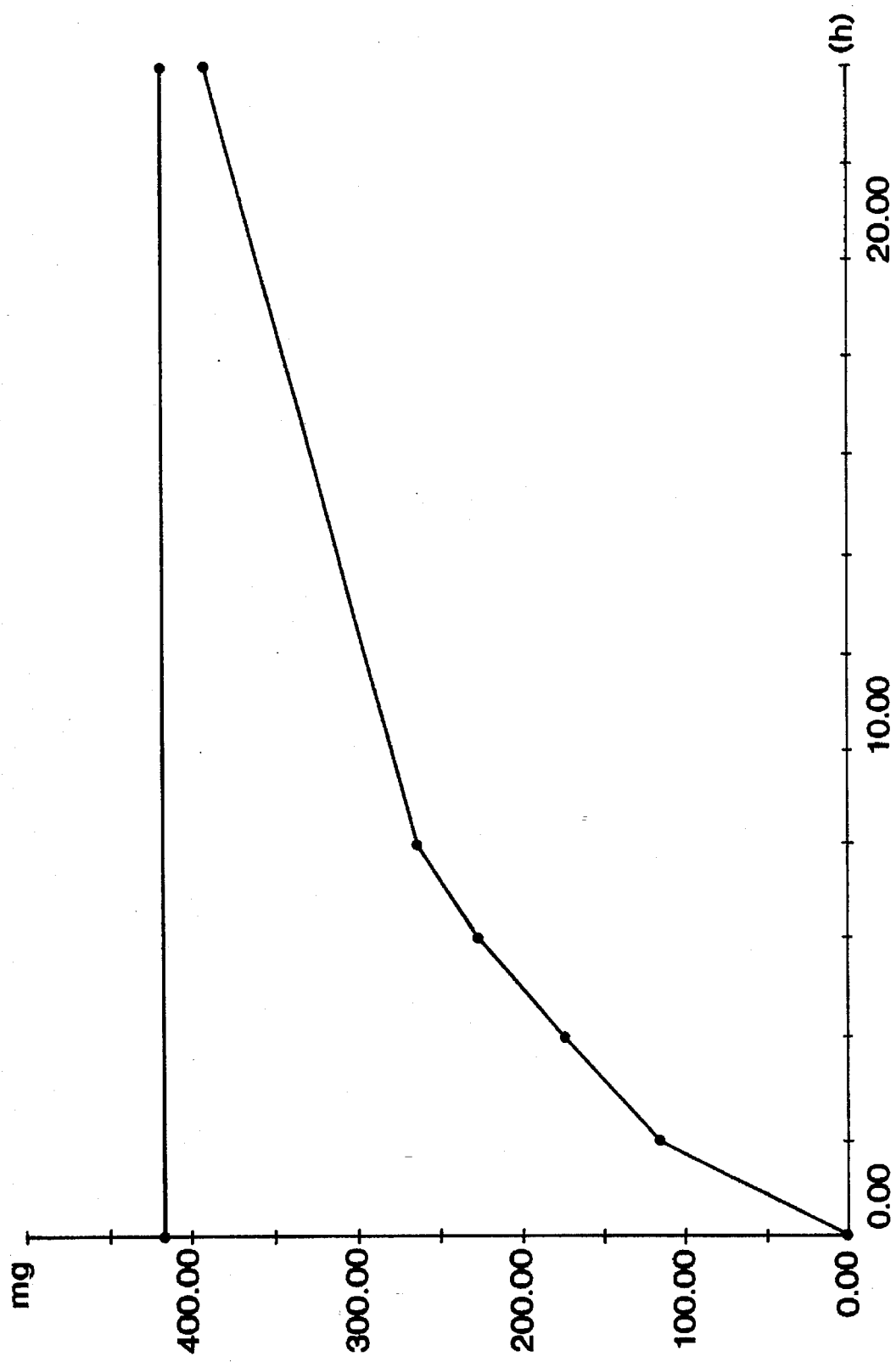
FIG. 7 The release kinetics of an inventive system according to example 1 in which the released active substance (mg) is plotted against time (h).

The theophylline release from the pressed article was tested in 600 ml of artificial gastric juice at 37° C. using the USP "Rotating Basket" method. It was found that the release took place completely in approximately 24 hours and after a relatively rapid delivery of approximately 270 mg of theophylline, i.e. approximately 64% of the theophylline in the first 8 hours, there was only a slow further delivery. The release test result is shown in FIG. 7.

EXAMPLE 2

409 mg of theophylline coated with 11 mg of an acrylic resin (sold under the trademark EUDRAGIT RL 100 of Rohm Pharma) are filled into a press or compression mould, pressed smooth and compressed to a constant volume of 0.74 ccm with the subsequently introduced 180 mg of polypropylene foam power (sold under the trademark ACCUREL EP 100 of Armak Co., 200 um). The pressed article has a density of 0.8 g/ccm and a theophylline content of 409 mg.

Figure 8:
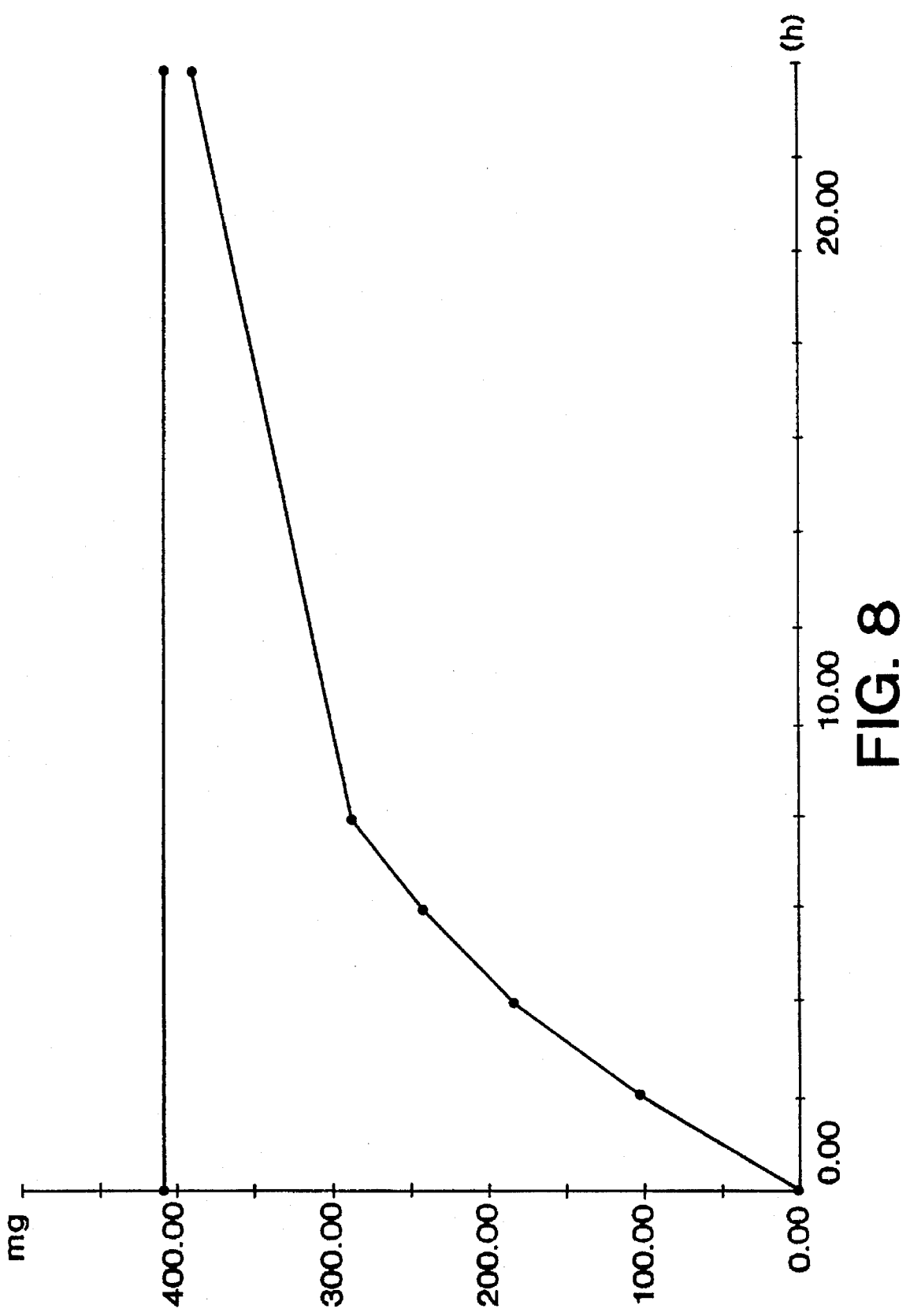
FIG. 8 The release kinetics of an inventive system according to example 2 in which the released active substance (mg) is plotted against time (h).

Theophylline release from the pressed article was tested in 600 ml of artificial gastric juice at 37° C. using the USP "Rotating Basket" method. It was found that the release was complete in approximately 24 hours and after a rapid delivery of approximately 300 mg of theophylline at a relatively constant speed, i.e. approximately 70% of the theophylline in the first 8 hours, there was subsequently only a slow further release. The result of the test is shown in FIG. 8.

EXAMPLE 3

409 mg of theophylline coated with 11 mg of an acrylic resin (EUDRAGIT RL 100 of Rohm Pharma) are filled into a compression mould, pressed smooth and compressed to a constant volume of 0.74 ccm together with a correspondingly punched polypropylene foam sheet (ACCUREL). The pressed article has a density of 0.8 g/ccm and a theophylline content of approximately 409 mg.

Figure 9:
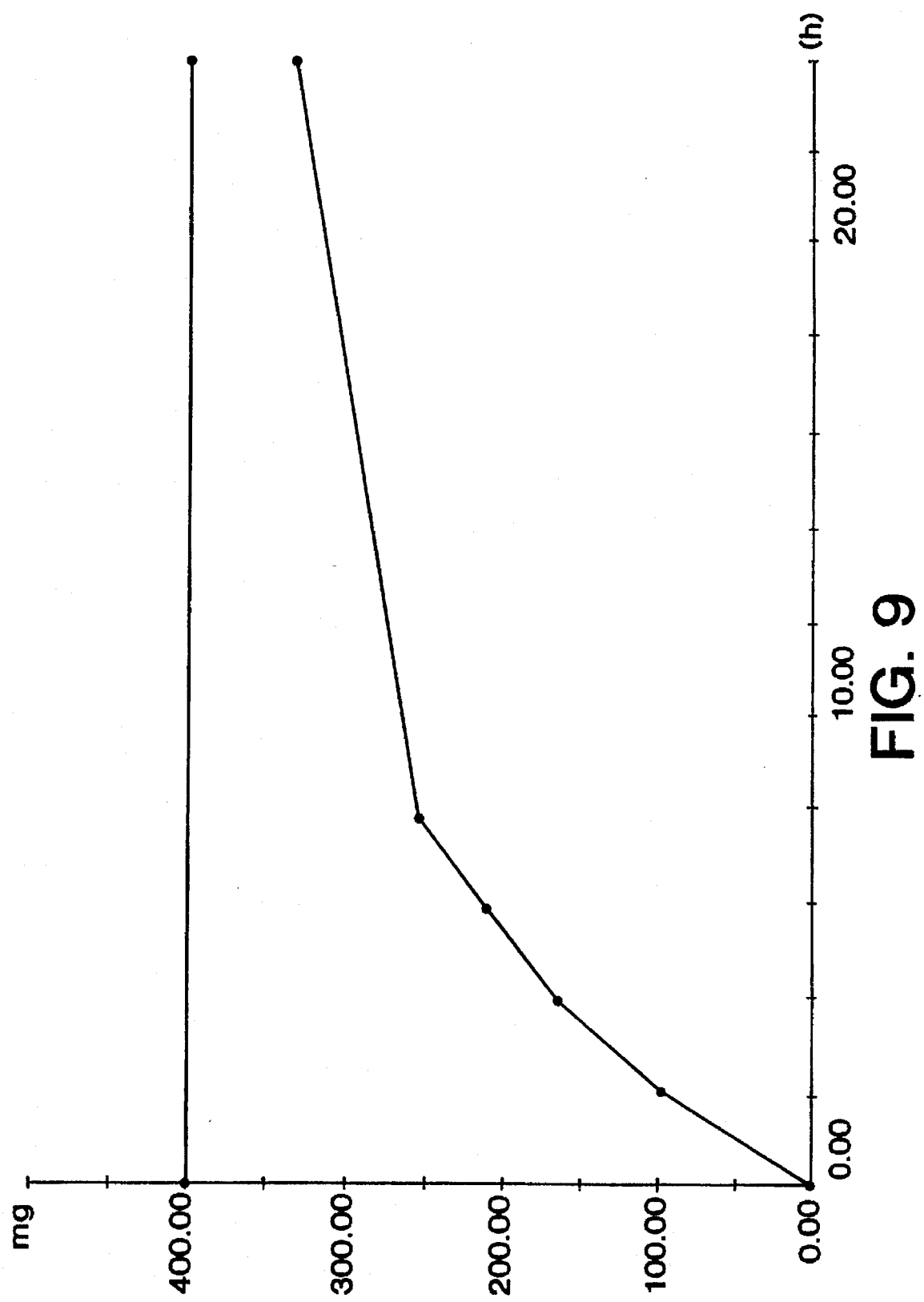
FIG. 9 The release kinetics of an inventive system according to example 3 in which the released active substance (mg) is plotted against time (h).

The theophylline release from the pressed article was tested in 600 ml of artificial gastric juice at 37° C. using the USP "Rotating Basket" method. Following a rapid delivery of in all approximately 250 mg of theophylline, i.e. approximately 60% of the total theophylline in the pressed article at a relatively constant speed during the first 8 hours, there was subsequently only a slow further delivery. The test result is shown in FIG. 9.

EXAMPLE 4

By decomposition granulation (wet granulation) 900 mg of a shaken granular material of particle size 15 mesh/ASTM with the following composition are prepared: 430 mg of theophylline, 172 mg of polypropylene foam powder (ACCUREL EP 100, <200 μm which has a pore diameter in the range of between 0.2 and 100 micrometers), 298 mg of an acrylic resin (EUDRAGIT RS 100 obtainable from Röhm Pharma). This granular material was filled into a commercially available gelatin capsule No. 00 (sold under the trademark CAPSUGEL of Werner Lambert Co.), so that each capsule contained approximately 430 mg of theophylline.

Figure 10:
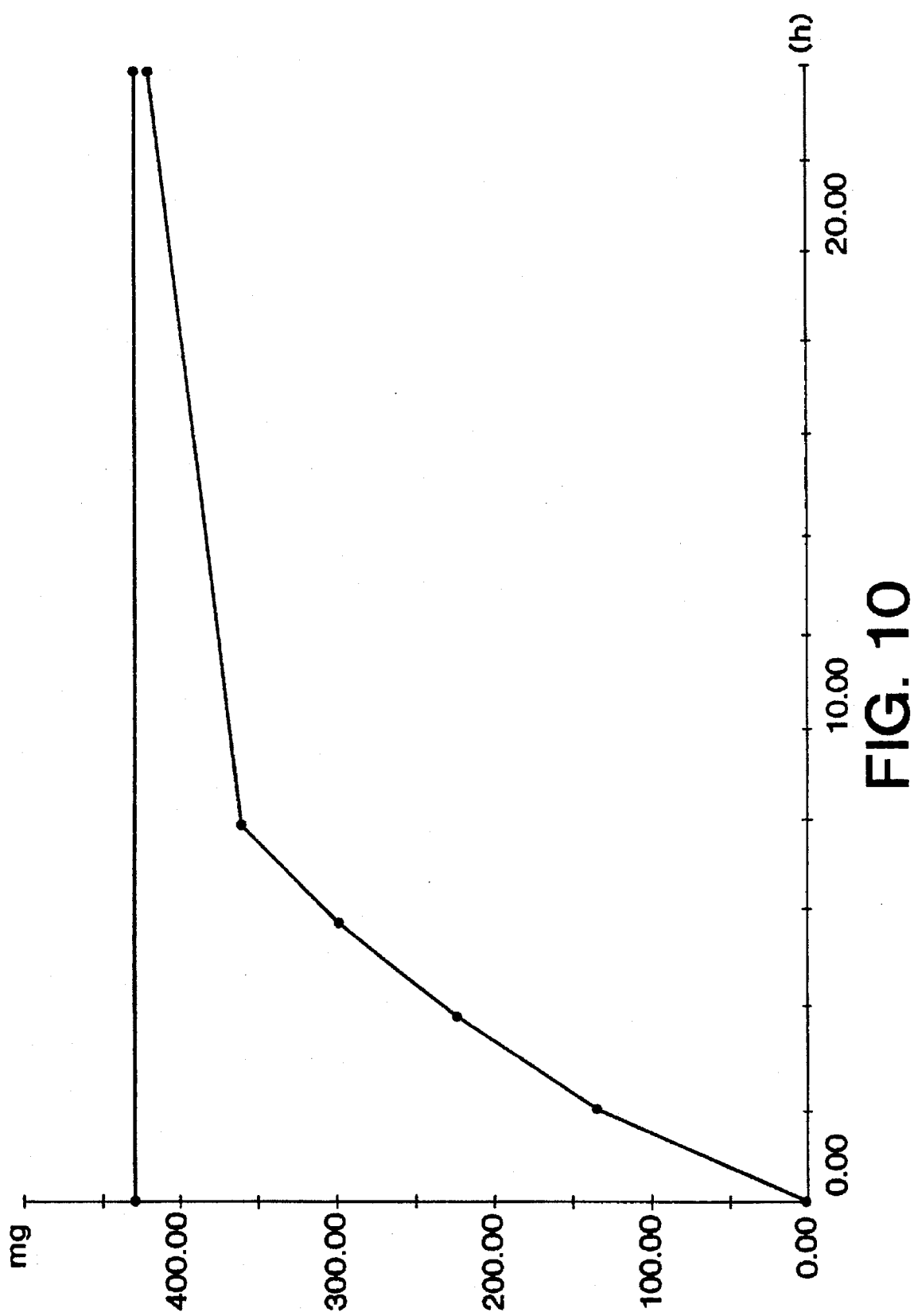
FIG. 10 The release kinetics of an inventive system according to example 4 in which the released active substance (mg) is plotted against time (h).

In order to test the theophylline release from this administration form, the granular material-filled capsule was tested in 600 ml of artificial gastric juice at 37° C. using the USP "Rotating Basket" method. It was found that after a rapid delivery of in all approximately 350 mg of theophylline, i.e. approximately 81% of the total theophylline in the product within 8 hours and at a relatively constant speed, there was subsequently only a slow further delivery. The test results are shown in FIG. 10.

EXAMPLE 5

To a homogeneous mixture melted at 100° C. of 7 g of beeswax, 10.5 g of carnauba wax, 17.5 g of polyisobutene (BASF OPPANOL B 15/1), 10 g of a nonionic surfactant based on polyethylene glycol esters of long-chain alcohols (BRIJ 700 of Atlas Chemie) and 2 g of polyethylene glycol (PEG 400) are added, accompanied by intense stirring, firstly 3 g of water soluble cellulose ether sold under the trademark TYLOPUR MHB 3000 P of Hoechst Aktiengesellschaft and 35 g of theophylline, followed by 2.5 g of hollow glass spheres (Q-CEL 500, a trademark of Philadelphia Quartz Co.). The material is poured into a TEFLON mold (TEFLON is a trademark of E. I. DuPont for polytetrafluoroethylene) and cooled. By punching the individual oral therapeutic systems within each case approximately 150 mg of theophylline are obtained.

Figure 11:
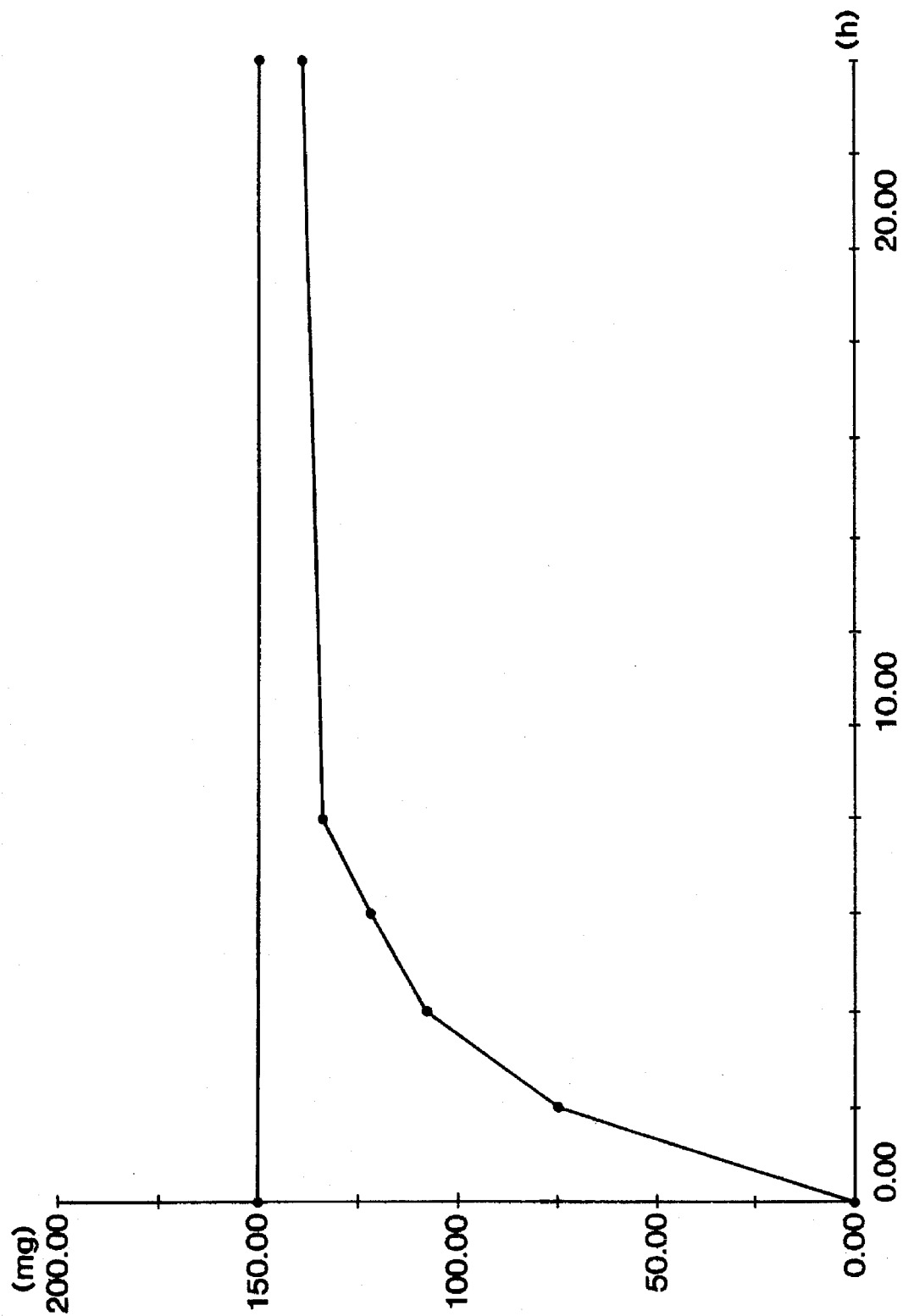
FIG. 11 The release kinetics of an inventive system according to example 5 in which the released active substance (mg) is plotted against time (h).

These oral systems are tested for theophylline release in 600 ml of artificial gastric juice at 37° C. using the USP "Rotating Basket" method. It was found that after a rapid delivery of in all approximately 125 mg of theophylline in the first 8 hours, i.e. 83% of the total theophylline in this product at a relatively constant speed, there was subsequently no further significant release. The results of this test are given in FIG. 11.

EXAMPLE 6

100 g of a hot melt material of 28.5 g of beeswax, 28.5 g of STAYBELITE ester resin (trademark of Hercules, Inc.) 10E, 20.0 g of theophylline, 10.0 g of polyethylene glycol (PEG 1000), 10.0 g of TYLOPUR MH 4000 P (water soluble cellulose ether by Hoechst Aktiengesellschaft) and 3.0 g of a nonionic surfactant based on polyethylene glycol ethers of long-chain alcohols (sold under the trademark BRIJ 76 of ATLAS CHEMIE) were sucked at 80° C., under vacuum, into a polypropylene hose manufactured under the trademark ACCUREL of Armak Co. (internal diameter 5.5 mm, external diameter 8.5 mm). After cooling, the single, oral therapeutic systems are obtained by cutting. The density of the systems produced was 0.65 g/ccm and they had a theophylline content of approximately 52 mg per unit.

Figure 12:
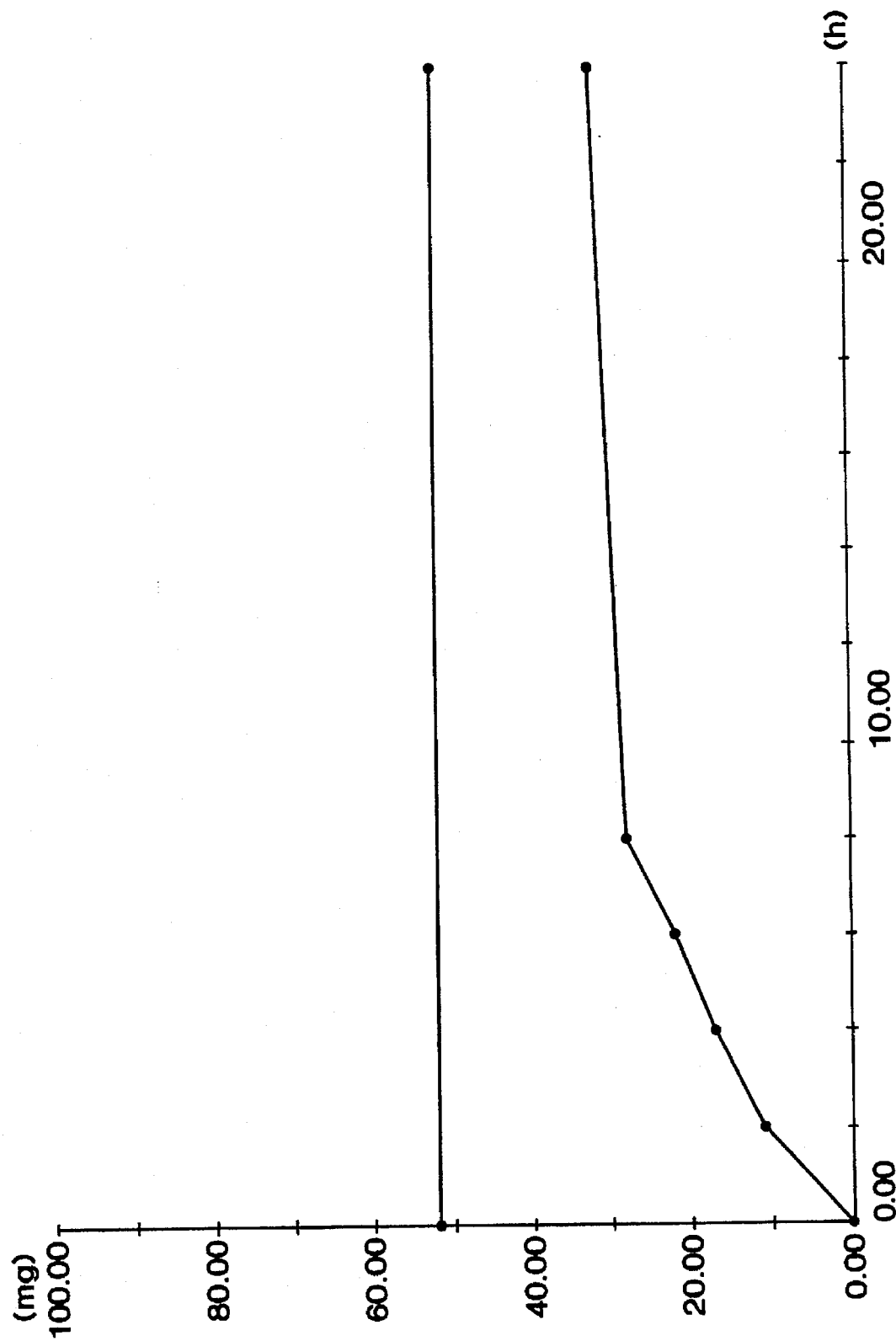
FIG. 12 The release kinetics of an inventive system according to example 6 in which the released active substance (mg) is plotted against time (h).

The theophylline release from these oral systems was tested in 600 ml of artificial gastric juice at 37° C. using the USP "Rotating Basket" method. It was found that following a rapid release over roughly 8 hours of approximately 30 mg of theophylline, i.e. 57% of the total theophylline in this product at a relatively constant speed, there was substantially no further significant release. The results of the test are given in FIG. 12.

We claim:

1. A therapeutic system for the oral administration of a medicament comprising a mixture of particles of the medicament in a therapeutically effective amount and a floatable aid part, wherein the floatable aid is a microporous foam material of a polymer selected from the group consisting of polyethylene, polypropylene, polyamide, polystyrene, polyester, polyacrylate, polytetrafluoroethylene, polyvinylchloride, polyvinylidene chloride, copolymers from the monomers on which said polymers are based and polysiloxane, wherein the floatable aid comprises a microporous foam material having a pore diameter of in the range of between 0.2 and 100 micrometers, wherein the microporous foam material does not contain the medicament within its pores, wherein the system delivers the medicament into gastric juices, and wherein the system floats in the gastric juices.

2. A therapeutic system according to claim 1, wherein the medicament is coated with a polymeric substance extrinsic from the microporous foam material.

3. A therapeutic system according to claim 1, wherein the system is constituted by a mixture consisting essentially of a drug as said medicament mixed with polymeric microporous foam material.

4. A therapeutic system according to claim 1, wherein the microporous material is distributed through the system by mixture with material forming the medicament part.

5. A therapeutic system according to claim 1, wherein the system disintegrates when contacting gastric juices into many small elements having micropores.

6. A therapeutic system for the oral administration of medicament comprising a medicament-containing part having a therapeutically effective amount of the medicament and a floatable aid part having a cavity-containing character, wherein the system delivers the medicament into the gastric juices, wherein the medicament is in physical contact with the floatable aid, wherein the floatable aid is a microporous foam material of a polymer selected from the group consisting of polyethylene, polypropylene, polyamide, polystyrene, polyester, polyacrylate, polytetrafluoroethylene, polyvinylchloride, polyvinylidene chloride, copolymers from the monomers on which said polymers are based and polysiloxane, wherein the floatable aid comprises a microporous foam material having a pore diameter of in the range of between 0.2 and 100 micrometers, wherein the microporous foam material does not contain the medicament within its pores, and wherein the floatable aid floats in the gastric juices.

7. The therapeutic system according to claim 6, wherein the medicament-containing part forms a hydrogel when in contact with gastric juices.

8. The therapeutic system according to claim 6, wherein the system is provided with a coating of the system for the controlled delivery of the medicament.

9. The therapeutic system according to claim 6, wherein the system is in the form of a tablet.

10. The therapeutic system according to claim 6, wherein the system is in the form of a foil.

11. A therapeutic system according to claim 6, wherein the medicament-containing part is a shaped body.

12. A therapeutic system according to claim 6, wherein the medicament-containing part is an extrudate.

13. A therapeutic system according to claim 6, wherein the medicament-containing part is a hot melt material.

14. The therapeutic system according to claim 6, wherein the floatable aid is formed of hollow elements.

15. The therapeutic system according to claim 6, wherein the floatable aid is an extrudate.

* * * * *